(12) United States Patent
Schoutens et al.

(10) Patent No.: US 8,500,739 B2
(45) Date of Patent: Aug. 6, 2013

(54) SECURING DEVICE TO SECURE FIXATION DEVICES TO BONE PORTIONS

(75) Inventors: Robert J. Schoutens, Basel (CH); Kan Naito, Chofu (JP); Ulrich Engenhardt, Basel (CH); Bruno Wiesmann, Inkwil (CH); Benjamin Straub, Village-Neuf (FR); Ralf Oesterlein, Friburg (DE)

(73) Assignee: DePuy Synthes Products, LLC, Raynham, MA (US)

( * ) Notice: Subject to any disclaimer, the term of this patent is extended or adjusted under 35 U.S.C. 154(b) by 1224 days.

(21) Appl. No.: 11/784,331

(22) Filed: Apr. 6, 2007

(65) Prior Publication Data

US 2008/0249532 A1    Oct. 9, 2008

(51) Int. Cl.
| A61B 17/56 | (2006.01) |
| A61B 17/84 | (2006.01) |
| A61B 17/88 | (2006.01) |
| B21F 11/00 | (2006.01) |

(52) U.S. Cl.
USPC ........... 606/86 R; 606/99; 606/103; 606/105; 606/324; 606/903; 140/123.6

(58) Field of Classification Search
USPC .................. 606/99, 86 B, 103, 263, 74, 86 R, 606/105; 140/123.6, 93.2; 254/199, 243, 254/245, 246, 256
See application file for complete search history.

(56) References Cited

U.S. PATENT DOCUMENTS

| 257,389 A | 5/1882 | Sager ............................. 30/134 |
| 1,304,620 A | 5/1919 | Steinkoenig et al. ......... 140/121 |
| 1,429,580 A | 9/1922 | Geiger ............................ 464/60 |
| 1,510,416 A | 9/1924 | Pietz et al. ..................... 606/205 |
| 1,561,119 A | 11/1925 | Smith .............................. 464/60 |
| 1,641,077 A | 8/1927 | Fouquet ......................... 140/121 |
| 2,049,936 A | 8/1936 | Zimmer .......................... 464/60 |
| 2,217,077 A | 10/1940 | Phillips .......................... 81/9.42 |
| 2,343,079 A | 2/1944 | Pickwell ......................... 464/60 |
| 2,447,319 A | 8/1948 | de Fourchambault ..... 192/70.21 |
| 2,480,783 A | 8/1949 | Sloan .......................... 29/896.91 |
| 2,875,779 A | 3/1959 | Campbell ..................... 137/529 |
| 3,021,129 A | 2/1962 | Maker .......................... 267/180 |
| 3,047,945 A * | 8/1962 | Logan ........................ 140/123.6 |
| 3,068,666 A | 12/1962 | Sabadash ....................... 464/60 |
| 3,169,560 A | 2/1965 | Caveney et al. ........... 140/123.6 |

(Continued)

FOREIGN PATENT DOCUMENTS

| DE | 28 24 071 A1 | 12/1978 |
| DE | 3124648 C2 | 5/1983 |

(Continued)

*Primary Examiner* — Michael T Schaper
(74) *Attorney, Agent, or Firm* — Woodcock Washburn LLP

(57) ABSTRACT

The present invention discloses a securing device that is used to secure a fixation device to two bone portions to promote healing between the two bone portions. The bone portions commonly include a skull bone portion and a skull bone flap or implant, and the fixation device is commonly a cranial clamp. The securing device provides for securing the fixation device in a uniform, single movement as opposed to currently available products. The securing device has two handles pivotably connected, and a gripping means moveably associated with one handle. As the handles are activated, the gripping means travels proximally along the one handle and grips an elongated section of the fixation device and exerts a tensioning force along the shaft of the elongated section prior to the cutting means cutting the elongated shaft to secure the fixation device in place.

25 Claims, 17 Drawing Sheets

U.S. PATENT DOCUMENTS

| | | | | |
|---|---|---|---|---|
| 3,370,621 A * | 2/1968 | Brohawn | | 140/123.6 |
| 3,376,727 A | 4/1968 | Hinden | | 29/243.521 |
| 3,390,546 A | 7/1968 | Jewell | | 464/78 |
| 3,537,275 A | 11/1970 | Smith | | 464/78 |
| 3,540,106 A | 11/1970 | Goldman | | 29/268 |
| 3,588,291 A | 6/1971 | Curwen et al. | | 417/417 |
| 3,645,302 A * | 2/1972 | Caveney et al. | | 140/93.2 |
| 3,763,560 A | 10/1973 | Makkay et al. | | 30/124 |
| 3,810,499 A * | 5/1974 | Benfer | | 140/123.6 |
| 3,906,774 A | 9/1975 | LaPointe | | 72/391 |
| 3,908,268 A | 9/1975 | Brown | | 30/124 |
| 4,050,464 A | 9/1977 | Hall | | 128/303 R |
| 4,202,384 A * | 5/1980 | Aubert | | 140/123.6 |
| 4,203,305 A | 5/1980 | Williams | | 64/15 R |
| 4,246,698 A | 1/1981 | Lasner et al. | | 30/134 |
| 4,321,952 A | 3/1982 | Natkins | | 140/93.2 |
| 4,367,746 A | 1/1983 | Derechinsky | | 128/325 |
| 4,395,824 A | 8/1983 | Puro | | 30/134 |
| 4,404,746 A | 9/1983 | Jansson et al. | | 30/124 |
| 4,449,429 A | 5/1984 | Sauer et al. | | 81/9.3 |
| 4,587,963 A | 5/1986 | Leibinger et al. | | 128/92 B |
| 4,627,164 A | 12/1986 | Mikic et al. | | 30/135 |
| 4,733,701 A * | 3/1988 | Loisel et al. | | 140/93.2 |
| 4,889,110 A | 12/1989 | Galline et al. | | 606/69 |
| 4,924,709 A | 5/1990 | Plyter | | 73/829 |
| 4,928,738 A * | 5/1990 | Hinnen et al. | | 140/93.4 |
| 4,932,638 A | 6/1990 | Chen | | 269/6 |
| 4,966,600 A | 10/1990 | Songer et al. | | 606/74 |
| 5,000,232 A * | 3/1991 | Wolcott | | 140/93.4 |
| 5,027,867 A | 7/1991 | O'Connor | | 140/123.5 |
| 5,048,575 A | 9/1991 | Smith | | 140/93.2 |
| 5,057,113 A * | 10/1991 | Mingozzi | | 606/103 |
| 5,083,350 A | 1/1992 | Sandreid | | 24/134 |
| 5,111,853 A | 5/1992 | Scruggs | | 140/123.6 |
| 5,116,340 A | 5/1992 | Songer et al. | | 606/103 |
| 5,167,582 A | 12/1992 | Hunt | | 464/78 |
| 5,268,001 A | 12/1993 | Nicholson et al. | | 606/72 |
| 5,312,410 A | 5/1994 | Miller et al. | | 606/86 |
| 5,323,521 A | 6/1994 | Freund et al. | | 29/243.527 |
| 5,345,663 A | 9/1994 | Scruggs | | 29/282 |
| 5,350,399 A | 9/1994 | Erlebacher et al. | | 606/213 |
| 5,361,475 A | 11/1994 | Scruggs | | 29/267 |
| 5,370,646 A | 12/1994 | Reese et al. | | 606/72 |
| 5,372,166 A * | 12/1994 | Lai | | 140/123.6 |
| 5,386,856 A * | 2/1995 | Moody et al. | | 140/123.5 |
| 5,388,619 A | 2/1995 | Ghawi | | 140/123.6 |
| 5,423,817 A | 6/1995 | Lin | | 606/61 |
| 5,449,361 A | 9/1995 | Preissman | | 606/103 |
| 5,476,465 A | 12/1995 | Preissman | | 606/61 |
| 5,511,589 A | 4/1996 | Scruggs | | 140/93.2 |
| 5,531,297 A | 7/1996 | Pipan | | 188/65.1 |
| 5,531,750 A | 7/1996 | Even-Esh | | 606/79 |
| 5,540,697 A | 7/1996 | Rehmann et al. | | 606/91 |
| 5,540,698 A | 7/1996 | Preissman | | 606/103 |
| 5,545,168 A | 8/1996 | Burke | | 606/74 |
| 5,569,253 A | 10/1996 | Farris et al. | | 606/74 |
| 5,600,878 A | 2/1997 | Byrne et al. | | 29/243.525 |
| 5,632,312 A | 5/1997 | Hoffman | | 140/123.6 |
| 5,666,710 A | 9/1997 | Weber | | 29/243.523 |
| 5,720,747 A | 2/1998 | Burke | | 606/74 |
| 5,743,310 A * | 4/1998 | Moran | | 140/123.6 |
| 5,749,899 A | 5/1998 | Bardin | | 606/232 |
| 5,832,964 A * | 11/1998 | Joshi | | 140/123.6 |
| 5,868,748 A | 2/1999 | Burke | | 606/74 |
| 5,902,305 A | 5/1999 | Beger et al. | | 606/103 |
| 5,925,050 A | 7/1999 | Howard, III | | 606/83 |
| 5,928,244 A | 7/1999 | Tovey et al. | | 606/104 |
| 5,935,130 A | 8/1999 | Kilpela et al. | | 606/74 |
| 5,944,302 A | 8/1999 | Loc et al. | | 267/180 |
| 5,966,815 A | 10/1999 | Sheikh | | 30/124 |
| 6,010,513 A | 1/2000 | Törmälä et al. | | 606/142 |
| 6,021,553 A | 2/2000 | Bieber et al. | | 29/243.521 |
| 6,203,437 B1 | 3/2001 | Durie et al. | | 464/78 |
| 6,368,326 B1 | 4/2002 | Dakin et al. | | 606/103 |
| 6,378,289 B1 | 4/2002 | Trudeau et al. | | 60/103 |
| 6,379,363 B1 | 4/2002 | Herrington et al. | | 606/79 |
| 6,526,661 B1 | 3/2003 | Shutts et al. | | 30/90.1 |
| 6,599,295 B1 | 7/2003 | Tornier et al. | | 606/104 |
| 6,641,588 B2 | 11/2003 | Citron et al. | | 606/103 |
| D488,229 S | 4/2004 | Rinner et al. | | D24/143 |
| 7,017,344 B2 | 3/2006 | Pellizzari et al. | | 60/517 |
| 7,037,311 B2 | 5/2006 | Parkinson et al. | | 606/99 |
| 7,048,737 B2 | 5/2006 | Wellisz et al. | | 606/70 |
| 7,048,738 B1 | 5/2006 | Wellisz et al. | | 606/70 |
| 7,059,362 B2 | 6/2006 | Koons et al. | | 140/123.5 |
| 7,060,067 B2 | 6/2006 | Needham et al. | | 606/61 |
| 7,063,110 B2 * | 6/2006 | Chen | | 140/123.6 |
| 7,063,704 B2 | 6/2006 | Citron et al. | | 606/80 |
| 7,089,970 B2 * | 8/2006 | Bernard | | 140/123.6 |
| 7,168,457 B2 * | 1/2007 | Bernard | | 140/123.6 |
| 7,299,830 B2 * | 11/2007 | Levin et al. | | 140/123.6 |
| 7,422,037 B2 * | 9/2008 | Levin et al. | | 140/123.6 |
| 7,806,895 B2 * | 10/2010 | Weier et al. | | 606/74 |
| 8,096,999 B2 * | 1/2012 | Nesper et al. | | 606/105 |
| 2002/0016593 A1 | 2/2002 | Hearn et al. | | 606/72 |
| 2002/0169455 A1 | 11/2002 | Bannerman et al. | | 606/99 |
| 2003/0193046 A1 * | 10/2003 | Chen | | 254/243 |
| 2005/0137608 A1 | 6/2005 | Hearn et al. | | 606/103 |
| 2005/0268983 A1 * | 12/2005 | Levin et al. | | 140/123.6 |
| 2006/0064110 A1 | 3/2006 | Nesper et al. | | 606/105 |
| 2007/0260251 A1 * | 11/2007 | Weier et al. | | 606/74 |
| 2007/0261754 A1 * | 11/2007 | Crittenden | | 140/93.2 |
| 2009/0044709 A1 * | 2/2009 | Hillegonds et al. | | 100/30 |
| 2012/0067450 A1 * | 3/2012 | Shafer et al. | | 140/123.6 |
| 2012/0197256 A1 * | 8/2012 | Knueppel | | 606/74 |

FOREIGN PATENT DOCUMENTS

| | | |
|---|---|---|
| DE | 298 12 988 U1 | 11/1998 |
| DE | 198 32 798 C1 | 11/1999 |
| EP | 0 372 306 A1 | 6/1990 |
| EP | 0 452 623 A1 | 11/1994 |
| EP | 0 857 466 B1 | 6/2002 |
| FR | 776041 | 1/1935 |
| FR | 1501311 | 11/1967 |
| FR | 2 480 376 | 10/1981 |
| FR | 2 717 674 | 9/1995 |
| FR | 2 777 449 | 10/1999 |
| GB | 206298 | 11/1923 |
| GB | 284014 | 1/1928 |
| GB | 1125739 | 8/1968 |
| GB | 1587370 | 4/1981 |
| GB | 2 226 618 A | 7/1990 |
| WO | 83/00010 A1 | 1/1983 |
| WO | 95/05127 A2 | 2/1995 |
| WO | 02/09602 A1 | 2/2002 |
| WO | 02/089659 A2 | 11/2002 |
| WO | 2004/016187 A2 | 2/2004 |
| WO | 2004/075765 A1 | 9/2004 |
| WO | 2006/066119 A1 | 6/2006 |

* cited by examiner

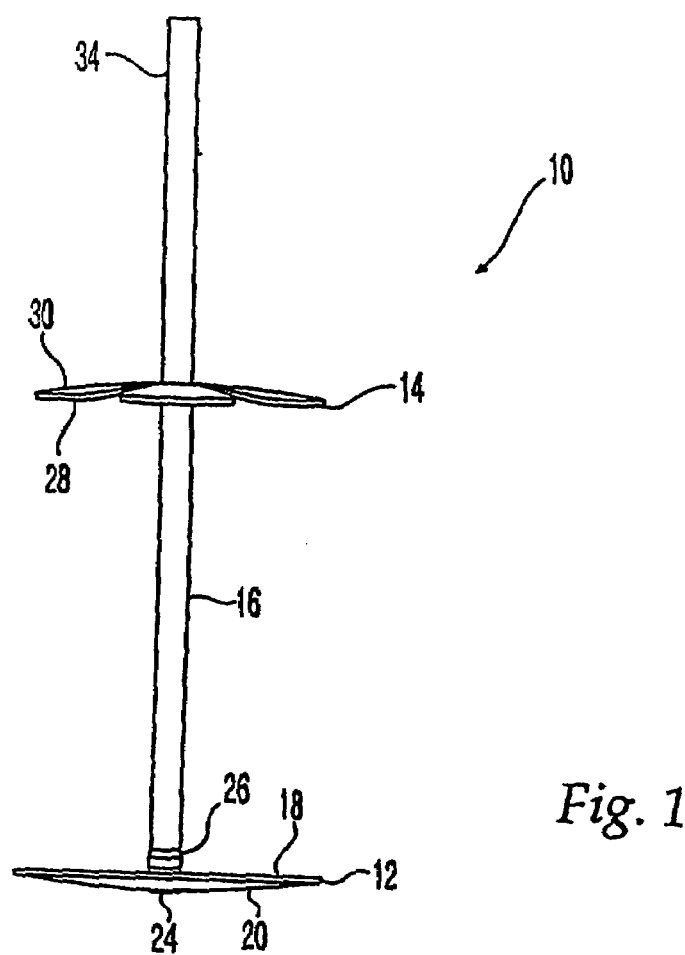
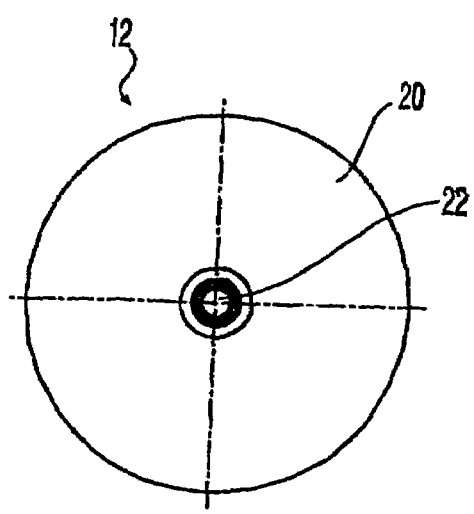
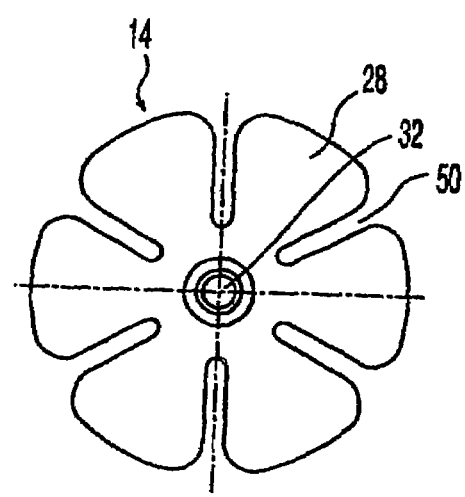
Fig. 1
Fig. 2
Fig. 3

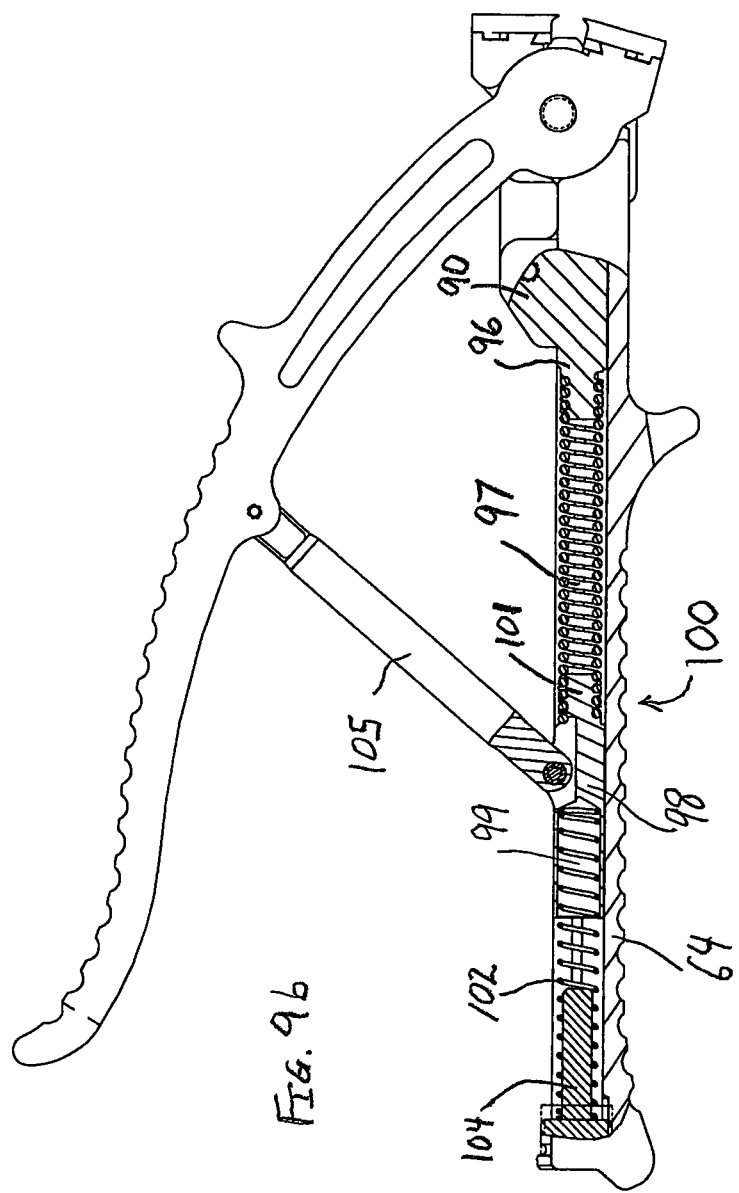

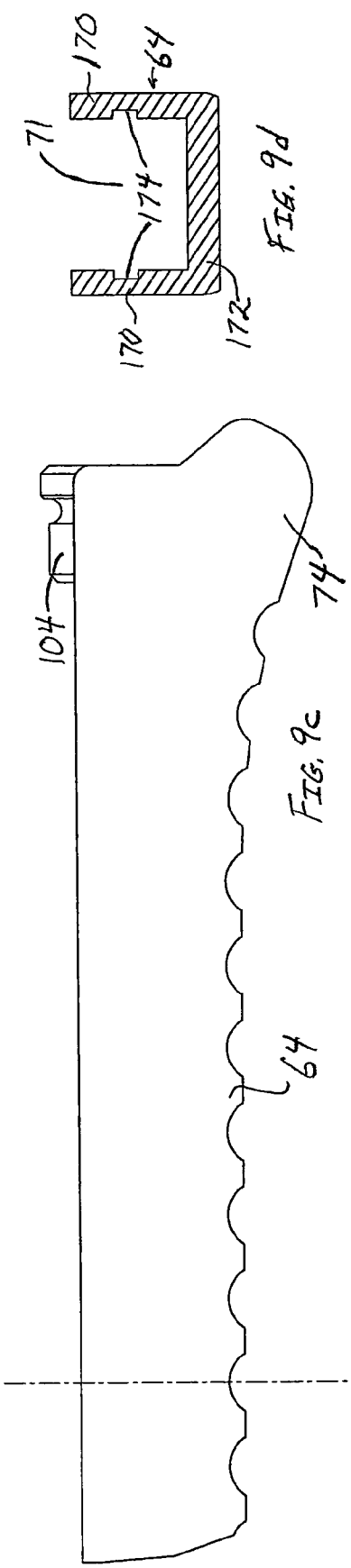

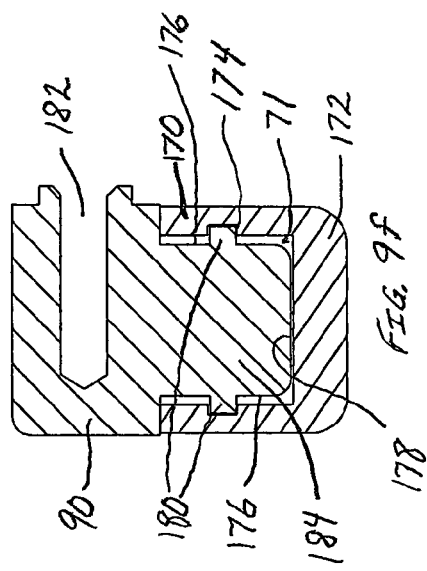
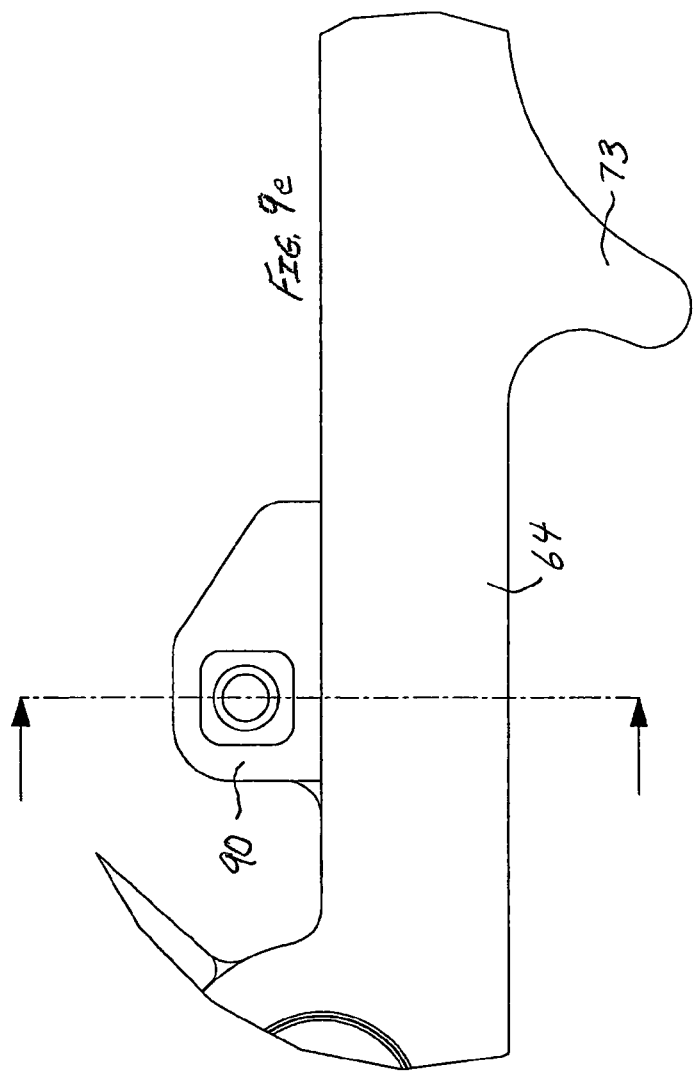

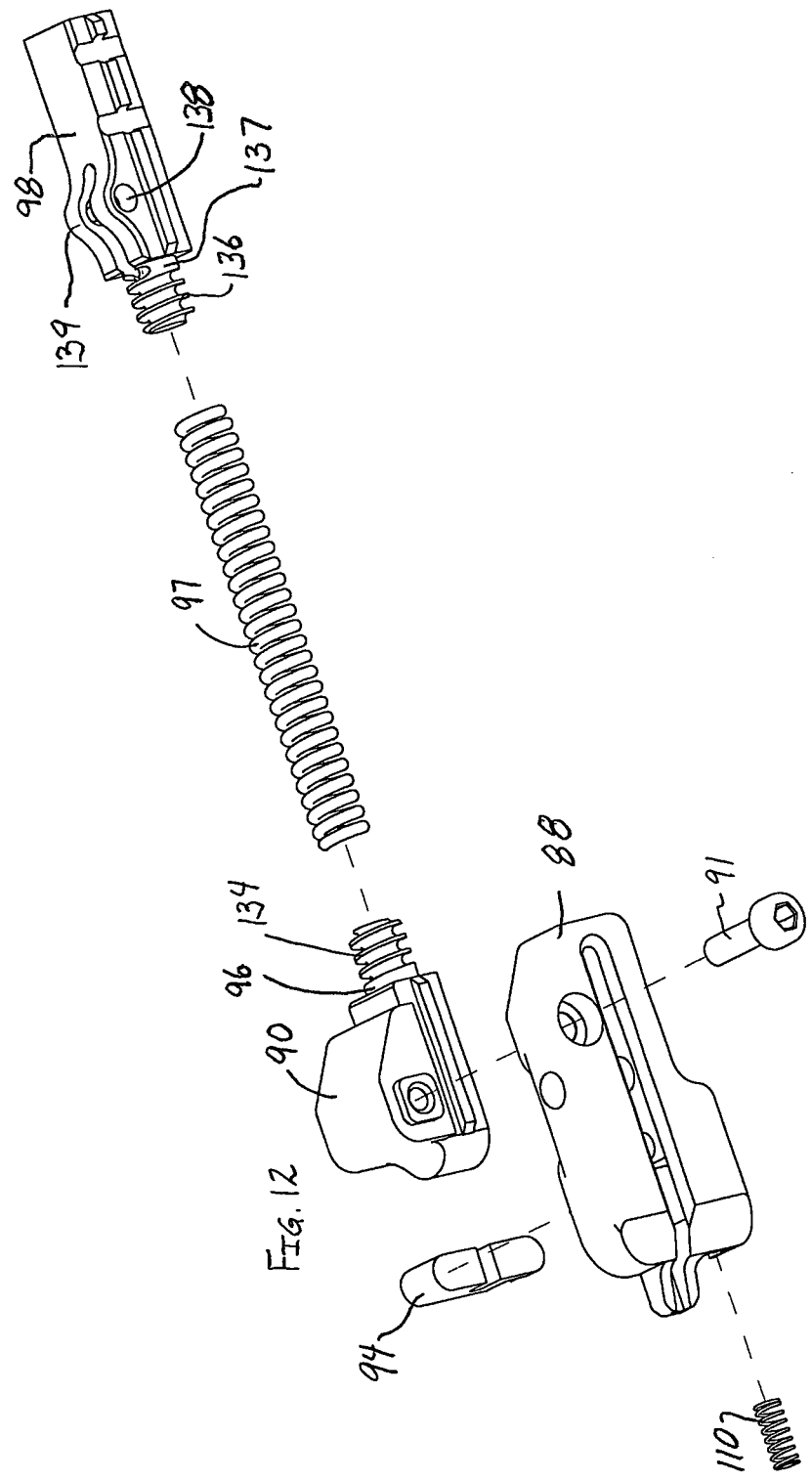

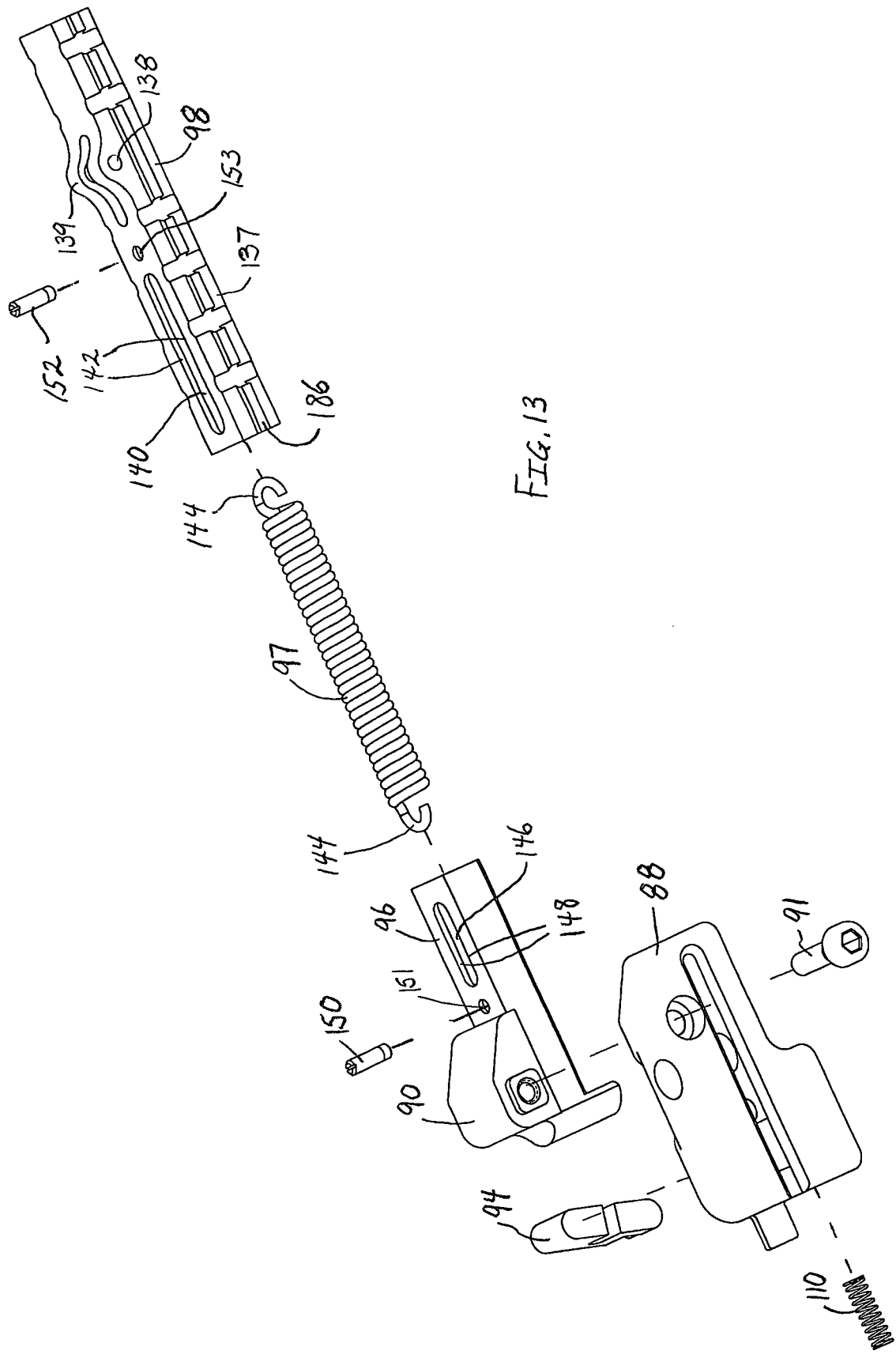

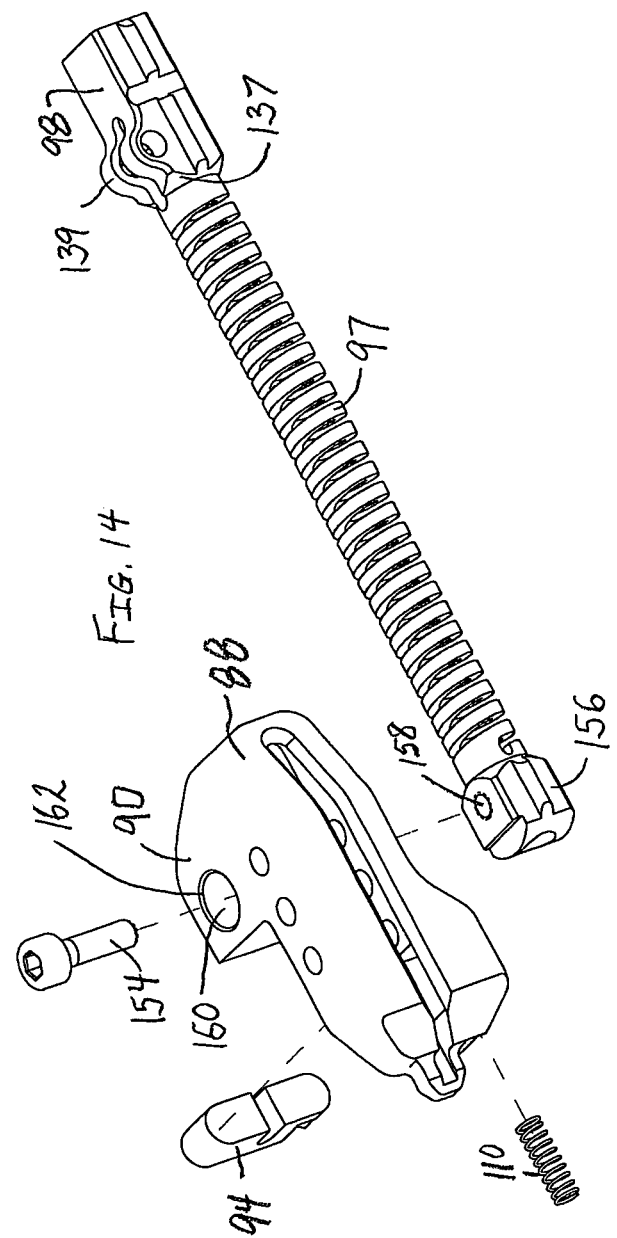

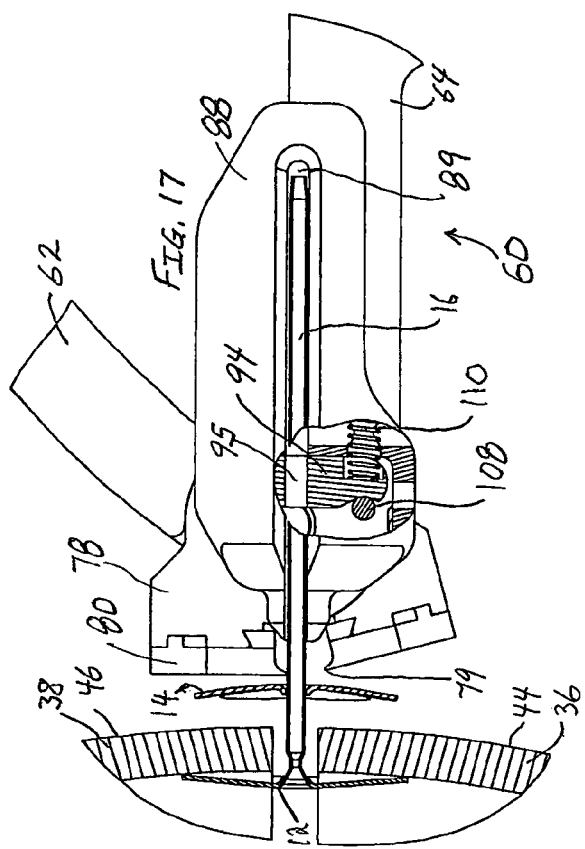
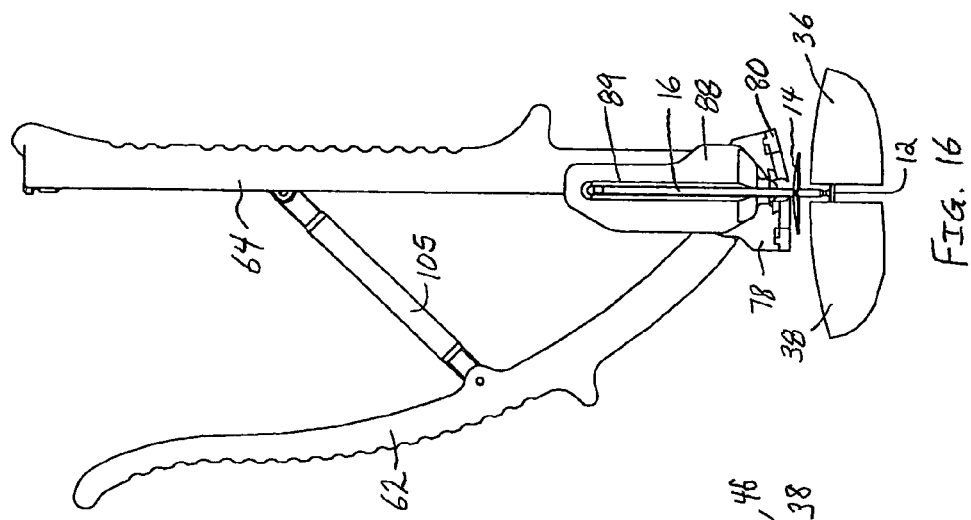
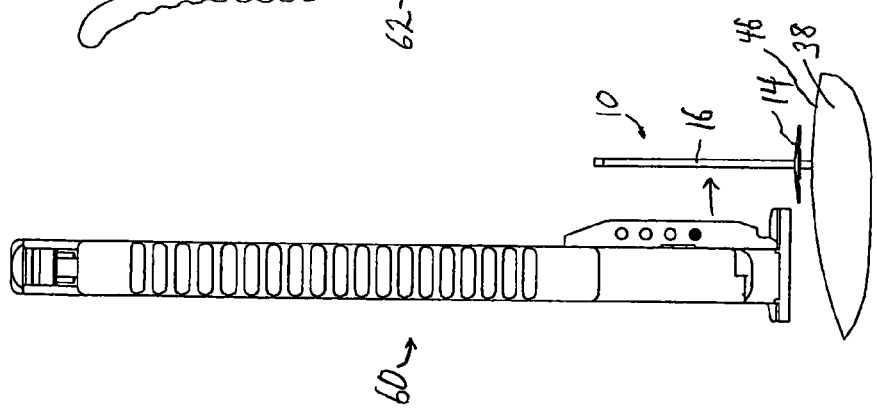

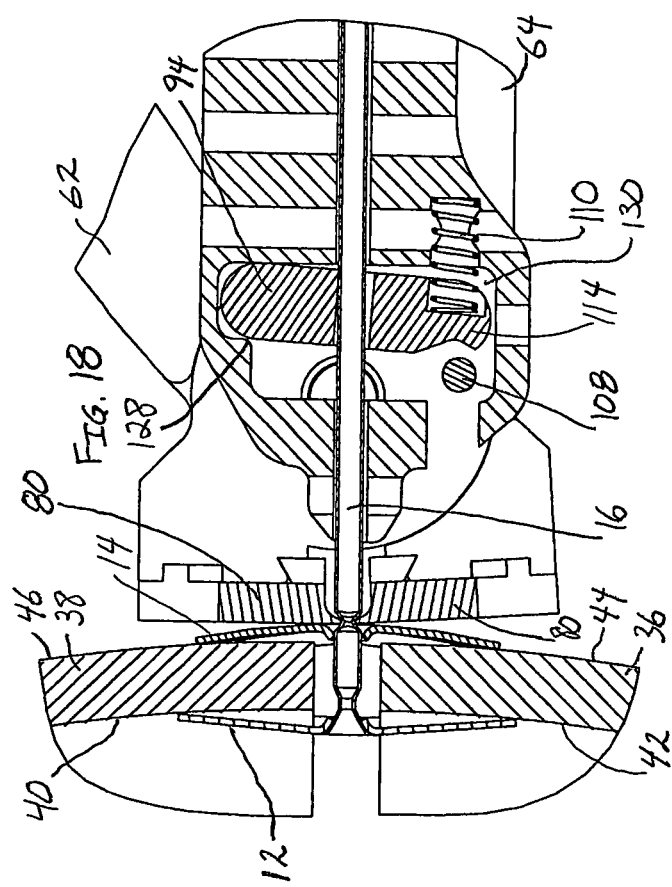

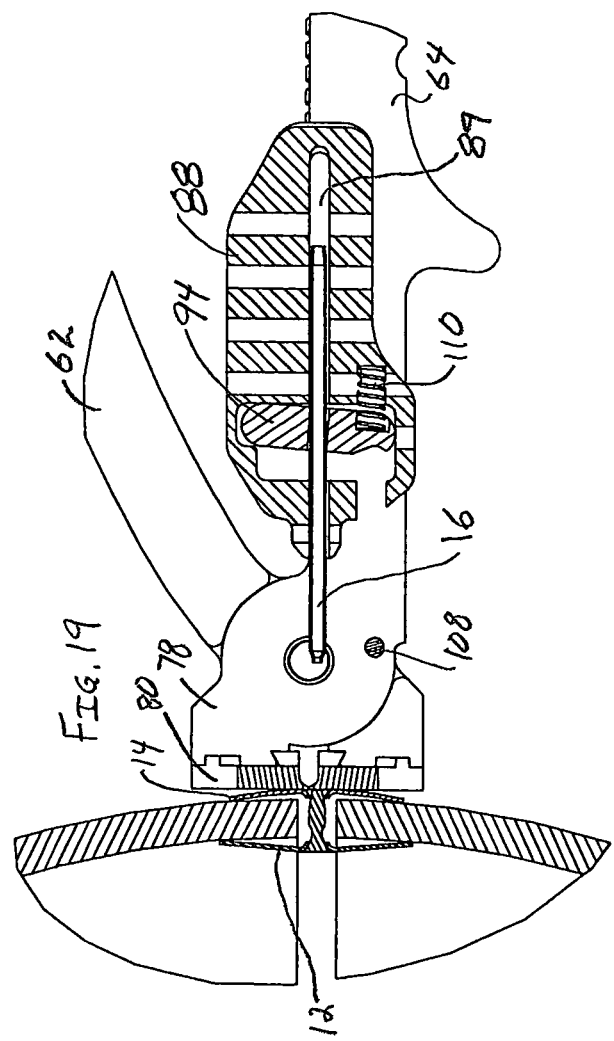

US 8,500,739 B2

SECURING DEVICE TO SECURE FIXATION DEVICES TO BONE PORTIONS

FIELD OF THE INVENTION

The present invention is directed to an instrument for use with a fixation device for soft tissue to bone or bone to bone fixation such as affixing a bone flap or bone implant to a bone.

BACKGROUND OF THE INVENTION

There are various surgical procedures that require fixing soft tissue to bone or bone to bone to produce healing such as fixing a bone flap or bone implant to a patient's skull. For example, craniotomies are surgical procedures conducted to treat various brain injuries, including tumors and aneurysms. As part of a craniotomy procedure, the surgeon creates an opening in the skull. One technique is to drill several adjacent holes to define the periphery of the opening and then using a tool to cut between the holes. The surgeon can either remove an entire section of the skull, or cut a sufficient amount to bend the skull away to allow access to the brain or head region. The cut-out section is commonly referred to as a bone flap. In other cases, an implant may be required to replace a section of the skull that is missing. In both cases, the bone flap or implant must be secured or fixed to the surrounding skull.

There are alternative ways to affix the bone flap or implant known to those in the art. One method involves drilling adjacent holes into the skull and into the bone flap or implant, and then securing the two together by way of threading a wire or other material through the holes and securing the ends of the material. Another fixation method uses bone plates to span the gap between the skull portion and the bone flap or implant. The bone plates contain screw holes through which screws are driven to secure the plate.

Another way to achieve fixation is to use metal clamps to span the gap between the skull and the bone flap or implant. The clamps commonly have a tube post with a first circular disk or plate secured to the bottom of the post. Another disk, having an annular center hole floats along the shaft of the post. The surgeon places the post between the skull and the bone flap or implant with the bottom plate below the skull and bone flap or implant and the other disk above those two pieces. An instrument is then used to hold the post and force the two plates together to secure the skull and bone flap or implant. The instrument usually has cutting blades on the end that first deform and then shear the post tube. An example of such a clamp system and an instrument for securing the clamps is described in WO 2006/066119.

The clamp system technique has many benefits over the other techniques, but there exists room for improvement of the instrument used to secure the clamps to the skull. The instrument should be easy to handle and not require excessive force to tension the clamp system or to shear the post tube.

SUMMARY OF THE INVENTION

The present invention concerns a securing device that can be used to secure a fixation device used to fix a bone portion to another bone portion or to soft tissue. The bone portion can be a bone (such as the skull bone), a bone flap (such as a skull bone flap), or a bone implant (such as a skull bone implant). The fixation device is preferably a cranial clamp when one bone portion is the skull bone. The present invention also concerns methods for securing the fixation devices. The fixation devices that preferably are used in conjunction with the securing device have an elongated section resembling a tubular post, cable, wire, rod or pin that is connected, preferably integrally connected, to a bottom member or plate. The fixation device also has an upper member or plate that preferably slides along the elongated section above the bottom member.

In one embodiment, the securing device has a first handle and a second handle where the first handle is pivotably attached to the second handle. Both handles have a distal end and a proximal end and a hand gripping section. The securing device has a gripping means that is associated with the second handle, and preferably is connected either directly or indirectly to the second handle. In a preferred embodiment, the gripping means is moveably, preferably slidably, connected with the second handle. The gripping means is designed to grip the elongated section of the fixation device in a secure manner, and more preferably to retain that grip upon the elongated section until at least the elongated section is cut, and preferably even after the elongated section has been cut. For this embodiment, the securing device also has a tensioning means for exerting a proximally-acting force on the gripping means. The proximally-acting force actuates the gripping means and causes the gripping means to grip onto the elongated section of the fixation device. The proximally-acting force also causes the gripping means to move, preferably to slide, proximally along the second handle. The device also contains a cutting means affixed at the distal end of each of the first and second handles for cutting the elongated section of the fixation device. In this embodiment, the physician, by activating the handles, causes the tensioning means to activate the gripping means whereby the gripping means grips onto the elongated section of the fixation device. Further force to the handles causes the proximally-acting force to pull on the gripping means and to pull the elongated section proximally ultimately exerting a tension force on the elongated section to secure the elongated section in a tight fit to the bone or skull area. Further force to the handles causes the cutting means to cut the elongated section to secure the fixation device in place.

In another embodiment, the securing device comprises a first handle and a second handle where the first handle is pivotably attached to the second handle and both the first handle and the second handle have a distal end, a proximal end, and a hand gripping portion in between. The device includes a gripping member that has an outer surface, a proximal portion and a distal portion. The gripping member is moveably connected, preferably slidably connected, with the second handle. The gripping member is also configured and dimensioned to grip onto the elongated section of the fixation device. The securing device of this embodiment also has a tensioning element that has a distal end and a proximal end with the distal end of the tensioning element being connected to the proximal portion of the gripping member. The securing device also has cutting blades that are affixed at the distal end of each of the first and second handles. The pivoting of the first and second handles causes the gripping member to grip the elongation section of the fixation device and to move, most preferably to slide, proximally and causes the cutting blades to cut the elongated section of the fixation device.

In an exemplary embodiment, the gripping member of the securing device has a slotted plate located within the gripping member where the slot of the plate is aligned with an internal channel of the gripping member when the first and second handles are in an open position. The elongated section of the fixation device can be inserted into the channel of the gripping member and through the slotted plate at the beginning of the process. When the handles are activated, the slotted plate rotates within the gripping member to frictionally grip onto and secure the elongated section of the fixation device. In one embodiment, the securing device further comprises a pin located on the second handle to block the rotational movement of the slotted plate. In another embodiment, the securing device further comprises a spring located within the gripping member to urge the rotation of the slotted plate.

In an exemplary embodiment, the securing device has a channel within the second handle that preferably has a groove extending along at least a portion of the handle. The gripping member has a corresponding tongue such that the gripping member can slide within the second handle.

The present invention also provides for a method for securing a first bone portion to a second bone portion (or a first bone portion to soft tissue or a first bone portion to a bone implant) with a fixation device by way of the securing device in a single motion. The bone (or soft tissue or bone implant) portions have an upper surface and a lower surface. In practice, one bone portion typically is a bone flap or bone implant. In one embodiment of the method where two bone portions are to be secured together, a fixation device, having an elongated section, e.g., a post, cable, wire, rod, pin, tube, etc., and a lower member connected to the elongated section and an upper member slidably engaged on the elongated section, is inserted between the first bone portion and the second bone portion, wherein the lower member is positioned below the lower surface of the bone portions and the upper member is positioned above the upper surface of the bone portions and has an upper surface. The securing device is positioned onto the elongated section of the fixation device. The securing device can take the form of any of the devices described and claimed herein. During the process, closing the handles on the securing device causes, in one uniform movement, the gripping means to grip the elongated section of the fixation device and to pull the elongated section proximally and to create a tension force along the elongated section in the proximal direction. Upon further application of pressure to the handles the cutting means cut the elongated section at a point adjacent the upper surface of the upper member of the fixation device, which can be, for example, a cranial clamp.

In a preferred method, the closing of the handles on the securing device causes the following actions occur sequentially: (1) the gripping means grips the elongated section of the fixation device; (2) the elongated section is pulled proximally; and (3) the elongated section is cut.

The process is conducted with the securing device being held substantially perpendicular to the bone, e.g., skull. In this manner, the closing of the handles does not cause a rotating force to be applied to the elongated section of the fixation device and thus does not cause the elongated section to pivot about any point, particularly about a point adjacent the cutting means or blades and the top member or plate of the fixation device.

BRIEF DESCRIPTION OF THE DRAWINGS

FIG. 1 is a perspective view of one embodiment of a fixation device.
FIG. 2 is a top view of the lower device member or plate.
FIG. 3 is a top view of the upper device member or plate.
FIG. 9b is a partial cross section view of one embodiment of the securing device.
FIG. 9c is a side view of a handle of one embodiment of the securing device.
FIG. 9d is a cross section view of FIG. 9c.
FIG. 9e is a side view of a handle of one embodiment of the securing device.
FIG. 9f is a cross section view of FIG. 9e.
FIG. 12 is an assembly view of one embodiment showing the tension assembly of one embodiment of the securing device.
FIG. 13 is an assembly view of one embodiment showing the tension assembly of one embodiment of the securing device.
FIG. 14 is an assembly view of one embodiment showing the tension assembly of one embodiment of the securing device.
FIG. 15 is a perspective view showing the use of one embodiment of the securing device.
FIG. 16 is a perspective view showing the use of one embodiment of the securing device.
FIG. 17 is a partial cross section showing the use of one embodiment of the securing device.
FIG. 18 is a partial cross section showing the use of one embodiment of the securing device in the cutting mode.
FIG. 19 is a partial cross section showing the use of one embodiment of the securing device after the cutting mode.

DETAILED DESCRIPTION OF ILLUSTRATIVE EMBODIMENTS

Figure 4:
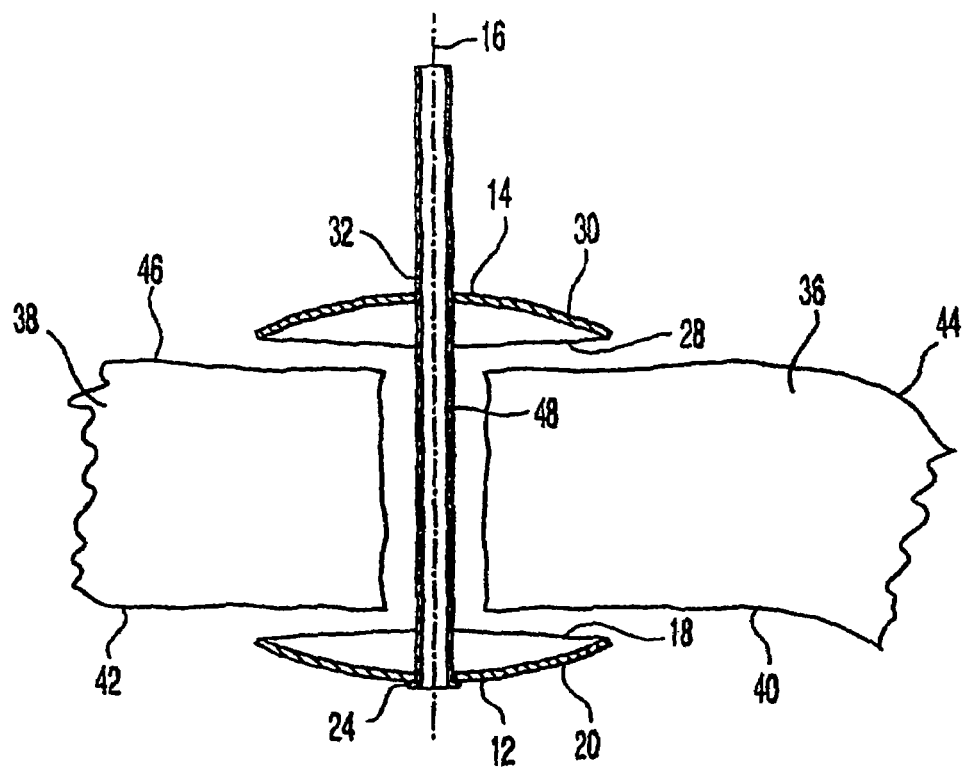
FIG. 4 is a cross sectional view of the fixation device in its implanted position prior to fixation.

The following description is intended to describe and concern the preferred embodiments for the present invention and is not to be construed as limiting the invention to the embodiments depicted for illustrative purposes.

The securing instrument of the present invention is designed to be used with any number of a variety of fixation devices for the fixation of soft tissue to bone or bone to bone to promote healing between the two. The bone to bone situation includes bone to bone implant and bone to bone flap situations as well. Commonly, the fixation device will take the form of any one of a variety of cranial clamps known in the art. A preferred cranial clamp design is depicted in FIGS. 1-5, and described in detail in PCT/US2005/045746 and US 2002/0016593 A1, which are hereby incorporated by reference in their entirety. For convenience and to avoid redundancy, the present invention is described below with respect to its use with a cranial clamp as the fixation device where the clamp has a post as the elongated section.

As depicted in FIGS. 1-5, the cranial clamp 10 has a post 16 and a bottom clamping member 12 secured to the post 16. A top or upper clamping member 14 slides along the shaft of the post 16. The clamp 10 and its components can be made from any suitable biocompatible material, such as stainless steel, titanium, or resorbable material.

The post 16 can be a tube or any other structure such as a cable, wire, rod or pin provided that it can be crimped as discussed below. The post 16 can be integral with the first clamping member 12. Alternatively, the post 16 can be fastened to the first clamping member 12 using any known conventional ways. For example, clamping member 12 can be provided with a bore 22 through which the post 16 is inserted. A head 24 can engage the edges of bore 22 for securing. An enlarged portion 26 of the post 16 can also be used to secure clamping member 12 to the post 16.

The bottom clamping member 12 preferably has a disk shape with a concave inner surface 18 and a convex outer surface 20, although other surface shapes can be used as well. Preferably, the bottom clamping member 12 has protrusions (not shown) extending upward to help grip the bottom portion of the skull or a bone flap or bone implant. For example, the protrusions can be in the form of punch throughs from the outer surface 20 to the inner surface 18, with the metal flared in quadrants extending upward. It is preferred that the outer surfaces 20, 30 for the bottom and upper members 12, 14 are substantially or fully smooth.

The top clamping member 14 also preferably has a disk shape with a concave inner surface 28 and a convex upper surface 30, while other shapes can be used as well. The top clamping member 14 has an opening 32 preferably at its center for slidably receiving the post 16. The top clamping member 14 preferably has a clover-leaf design as shown with recesses 50. To prevent the top member 14 from sliding off the post 16, the post 16 preferably has a flared portion 34.

The clamping members are shown in a disk shape, but the shape can be in any pattern desired for the application. The clamping members typically have a thin cross-section so that they can plastically deform to a certain extent under pressure during fixation.

In use, the cranial clamp 10 is used to fix a bone flap 36 to a skull 38 as depicted in FIG. 4. FIG. 4 shows the clamp 10 in a first position where at least a portion of the inner surface 18 of the clamping member 12 abuts an interior surface 40 of bone flap 36 and interior surface 42 of skull 38. In a similar way, at least a portion of inner surface 28 of clamping member 14 abuts an outer surface 44 of bone flap 36 and an outer surface 46 of skull 38. A portion of the post 16 fits within the gap 48 between the bone flap 36 and skull 38.

Figure 5:
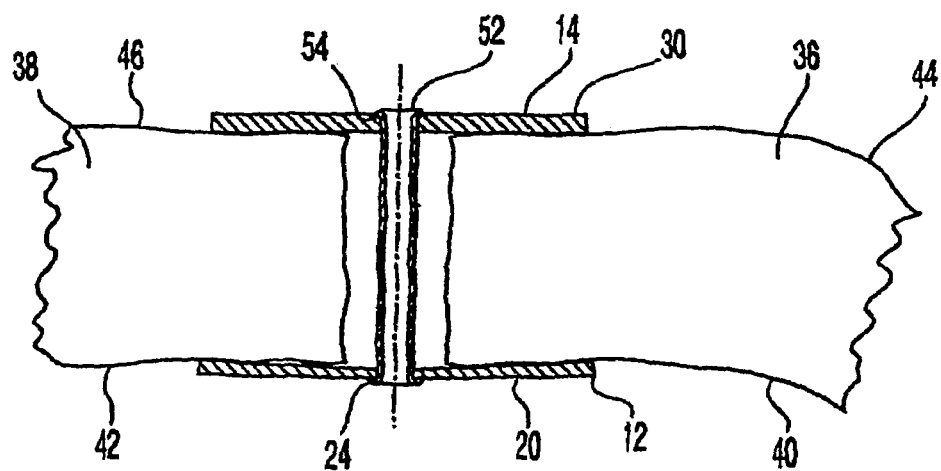
FIG. 5 is a cross sectional view of the fixation device in its implanted position after fixation.

After the cranial clamp 10 is secured or fixed in place, it looks as shown in FIG. 5. The clamp 10 is fixed in place by asserting an upward force on the post 16 (and thus on bottom clamping member 12) and asserting a downward force on the upper member 14. An instrument for accomplishing this task is part of the present invention as described below for the preferred embodiments.

A device is used to secure the cranial clamps 10 in place. A preferred embodiment for such a securing device 60 is presented in FIG. 6 in an assembly drawing, and in FIGS. 7-9 as well. The device 60 has an upper handle 62 and a lower handle 64, which handles are pivotably connected near the distal end of the handles by way of, for example, fastener 78. The upper handle 62 is preferably curved having a forward or distal portion 66, a proximal portion 67, and a handle portion 68, which is preferably curved slightly at its distal end and relatively flat through its mid-section and curved upwardly at its proximal portion 67 to act as a rest for the bottom of the hand. The handle portion 68 preferably has a textured gripping area 69 through its mid-section to enhance its feel. The upper handle preferably has a proximal lip 63 and a distal lip 65 to accommodate the hand. The lower handle 64 preferably has a forward lip 73 and a rear lip 74 to define a handle section in between for the hand. The lower handle 64 preferably is substantially straight throughout its length from its distal portion 70 to its proximal portion 72, but the lower handle 64 can also have recessed portions along its length to provide a more ergonomic feel, such as having two recessed portions separated by a central arching section. The lower handle 64 can also have a gripping surface formed integral therewith (such as shown in FIG. 8) or added onto the handle surface.

The lower handle 64 has a channel 71 formed by side walls 75 and bottom wall 77 (see FIG. 9*d*). The channel 71 houses a tensioning assembly for applying a tension force to the post 16 of the clamp 10. The tensioning assembly is described in more detail below.

Figure 6:
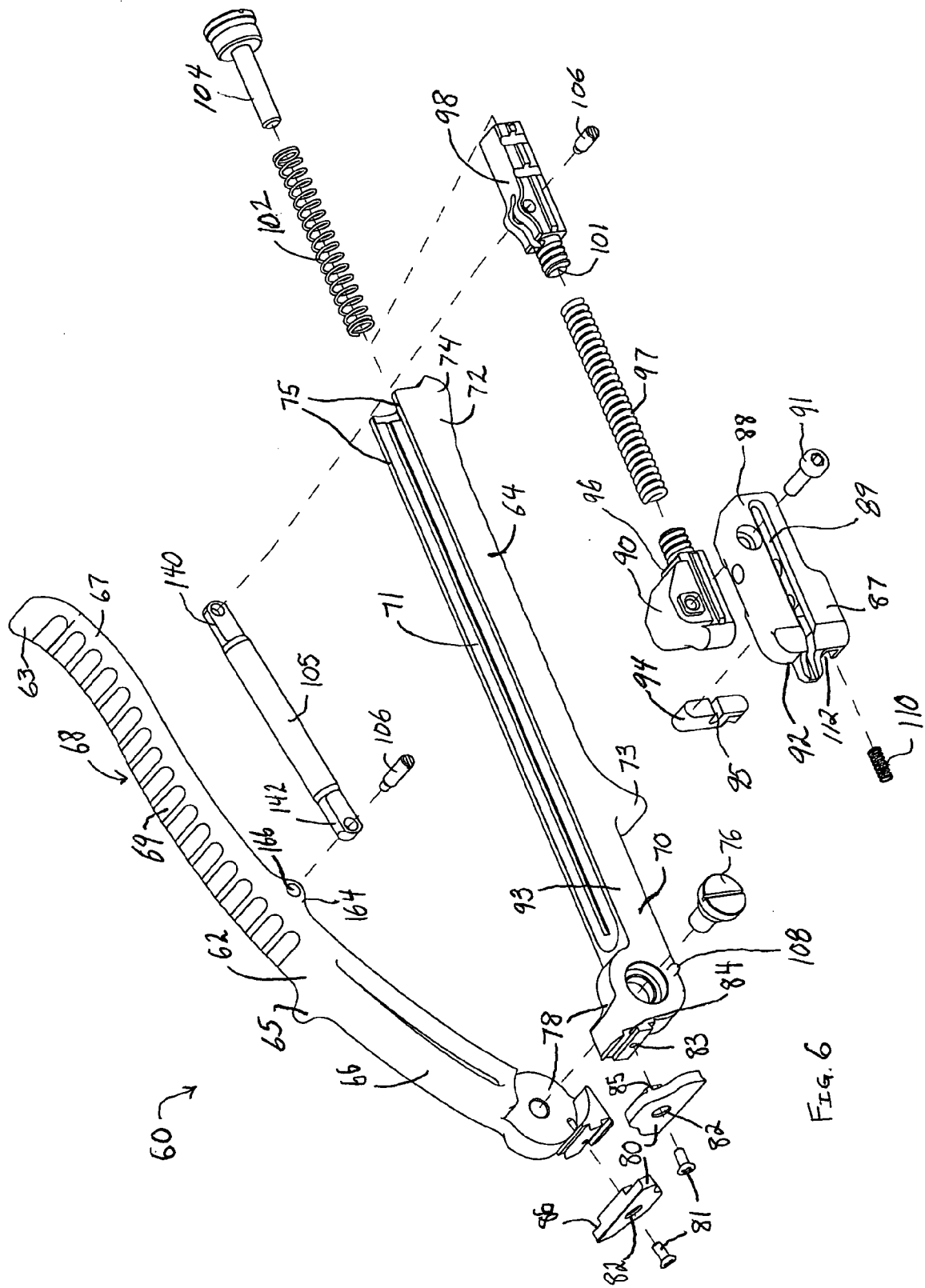
FIG. 6 is an assembly drawing of one embodiment of the securing device.

The handles 62, 64 are pivotally joined together at the distal end of the device 60. For example, as shown in FIG. 6, a pivot fastener 76 can be used for this purpose, but other means can also be used. The heads 78 for the handles are designed to mate with one another in a rotating fashion. The heads 78 preferably have a cutting means for cutting the post 16 of the cranial clamp 10. As depicted, the cutting means includes cutting blades 80. The cutting blades 80 have relatively sharp cutting edges 79 at their ends (see FIG. 8) for preferably first deforming and then shearing and/or cutting the post 16 of the clamp 10. The cutting blades 80 are secured to the handle heads 78, for example, by way of fasteners 81, such as screws, that are placed through a hole 82 in the cutting blades 80, and through a corresponding hole 83 in the heads 78. To aid in the securing of the cutting blades 80 to the heads 78, a groove 84 can be cut into the head 78 with a corresponding protrusion 85 on the inside surface 86 of the cutting blade 80.

The device 60 also includes a means for gripping the post 16 of the clamp 10. As depicted in FIG. 6, a preferred embodiment for this purpose includes a gripping block 88. The gripping block 88 has an inside surface 92 that is preferably designed to abut or fit beside the outer surface 93 of the lower handle 64 at the distal portion 70. The gripping block 88 is designed as a means for gripping the post 16 of the clamp 10. This function can be accomplished by any of various known mechanical ways.

The gripping block 88 is designed to have a means for accepting the post 16 of the clamp 10. For example, as depicted, the gripping block 88 has a groove 89 cut along the outer surface 87 of the gripping block; the groove 89 being dimensioned to accept the post 16 of the clamp 10. Preferably, the groove 89 extends substantially along the length of the gripping block, but does not extend entirely through the length of the gripping block although it can be designed to do so. In practice, the groove extends between about 0.5 to about 2.5 inches. Alternatively, the gripping block can simply have an opening at its distal end, like opening 103 (FIG. 10) into which the distal end of the post 16 can be inserted; in such a design, the groove 89 would instead be a bore hole 103 extending into the gripping block with no associated groove opening along the outer surface 87 of the gripping block 88 (in this design the securing device 60 would be slid onto the post 16 by way of hole 103). Thus, the gripping block 88 preferably has at least an internal channel, such as depicted by groove 89 (or by way of an elongated bore hole 103 through the block), for accepting the post 16.

The gripping means, depicted in the figures as the gripping block, also includes a means for gripping the post 16. In the preferred embodiment, located within a recess or cavity (shown in FIG. 11) within the gripping block 88, a slotted plate 94 is provided for this function. The slotted plate 94 contains a slot or groove 95, preferably near its mid-section, for accepting the post 16 of the clamp 10. The preferred design for the gripping block 88 is shown below in FIGS. 10-11.

The securing device 60 also has means for moving the gripping means proximally or away from the skull to assist in firmly seating the cranial clamp 10. In the preferred embodiment, a means for sliding the gripping block proximally along the lower handle 64 is provided for this function. As depicted in FIG. 6, a slider 90 is provided that can either be attached to, or formed integrally with, the gripping block 88 by fastening means such as fastener 91. If a separate slider 90 component is used in the design, it can be secured or connected to the gripping block 88 by any means. Alternatively, the gripping block/slider 88/90 can be formed as a unitary component. If a separate slider 90 component is used, preferably a protrusion can be formed on the outer surface of the slider 90 (not shown) and a corresponding groove formed into the outer surface of the gripping block 88 (not shown) to prevent rotation about the fastener 91. The protrusion/groove can be reversed between these two components, and is preferably located at or near the fastener 91.

The gripping means is connected to a means for pulling the gripping means proximally away from the skull. It is preferred that the gripping means travels proximally along the shaft of the one handle in a substantially perpendicular direction away from the bone surface and along the longitudinal axis of the elongated section of the fixation device. As depicted in the preferred embodiment, the proximal end 96 for the slider 90 is connected to a tensioning assembly 100 (see FIGS. 7 and 9b). In the embodiment depicted in FIG. 6, the tensioning assembly includes a tension spring 97 that is connected at its distal end to the proximal end of the slider 90 (and thus gripping block 88).

The securing device 60 has a means to actuate the tensioning assembly 100. As depicted in FIG. 6, a tension linkage 98 is connected at its distal end 101 to the proximal end of the tension spring 97. The distal end of the tension linkage 98 is connected at its proximal end to a return spring 102. An end cap screw 104 can be used to securely fasten the proximal end of the return spring 102 and to retain the tensioning means within the lower handle 64.

The upper handle 62, in the preferred embodiment depicted in FIG. 6, is used to generate the tension exerted upon the post 16 of the clamp 10 by the tensioning assembly 100. For example, the upper handle 62 can be attached to the tension linkage 98 housed within the channel 71 of the lower handle 64 by way of a linkage 105. The linkage 105 is attached to the upper handle 62 and tension linkage 98 by way of linkage fasteners 106 fitted through the upper end 142 and lower end 140, respectively, of the linkage 105.

Figure 7:
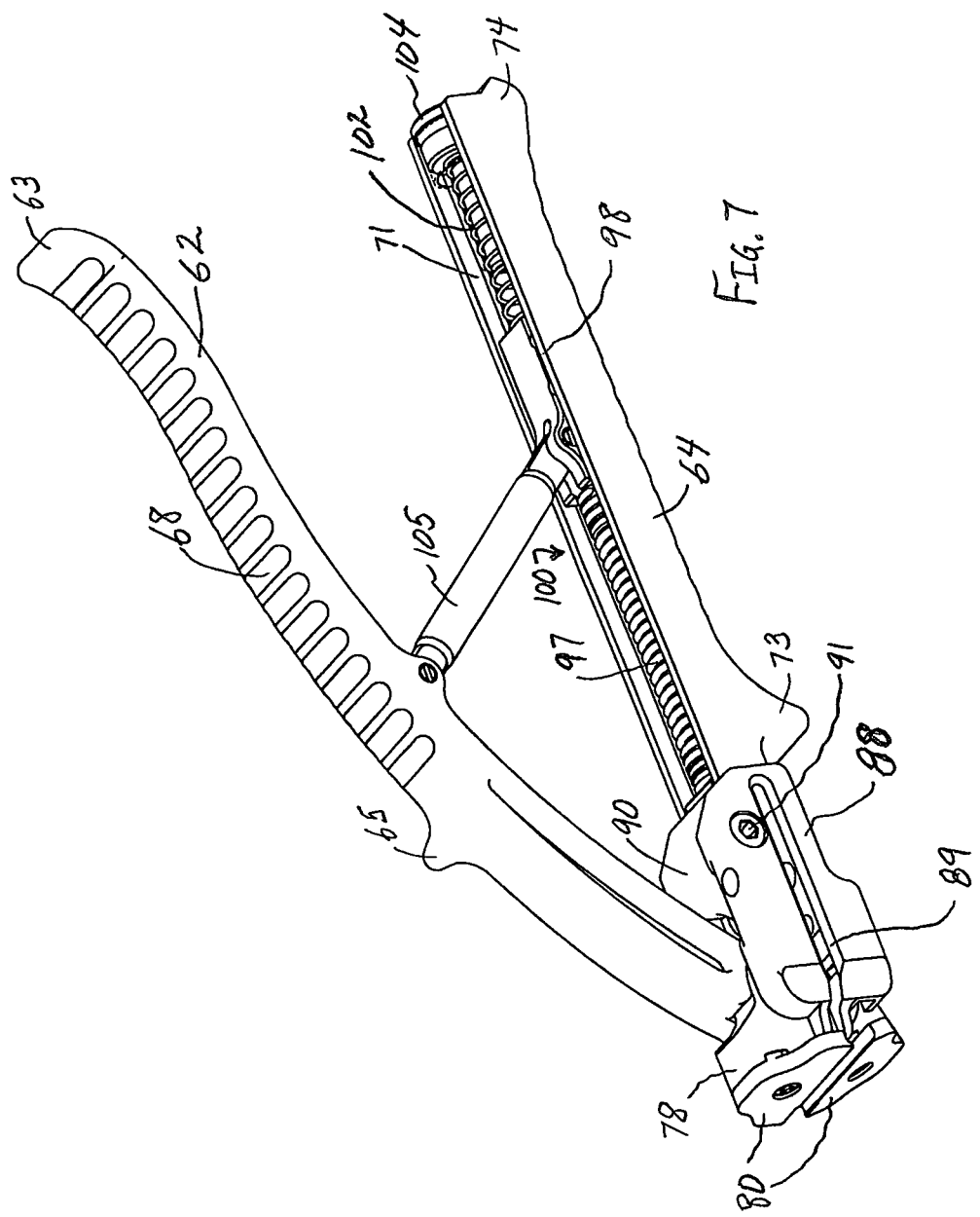
FIG. 7 is a perspective view of one embodiment of the securing device.
Figure 8:
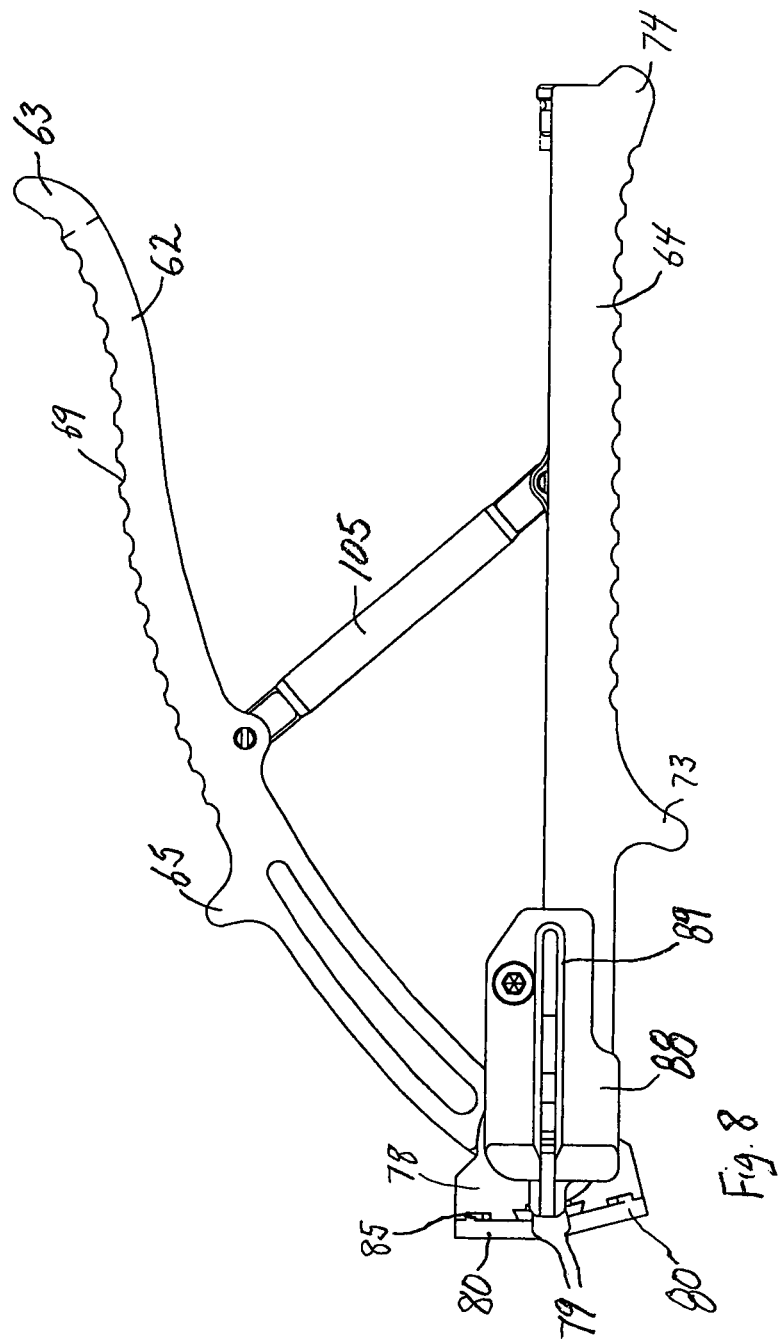
FIG. 8 is a side view of one embodiment of the securing device.
Figure 9A:
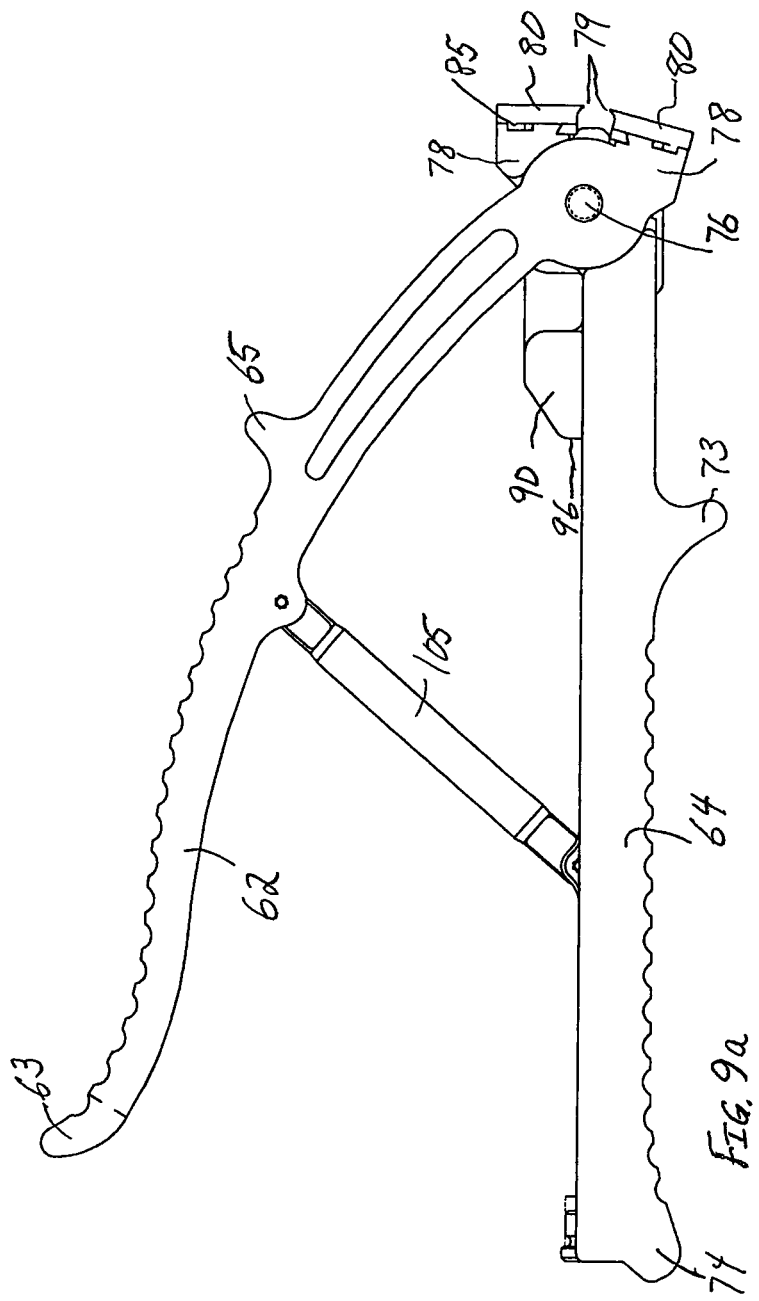
FIG. 9a is a side view of one embodiment of the securing device.

FIG. 7 shows a front-side view of the securing device 60 and FIG. 8 shows a side view of the device. FIG. 9a shows a back side view and FIG. 9b shows a partially-removed back side view. One embodiment for the tension assembly 100 is revealed in FIG. 9b, where it is shown that proximal end 96 of the slider 90 is designed to fit within the channel 71 of the lower handle 64 and connect to the distal end of the tension spring 97. The proximal end of the tension spring 97 is connected to the distal end 101 of the tension linkage 98, which is also designed to fit within the channel 71. The proximal end 99 of the linkage 98, which is also designed to fit within the channel 71 is connected to the distal end of the return spring 102, which has its proximal end connected to the distal end of the end cap screw 104.

The lower handle 64 is designed to guide the movement of the slider 90. In one embodiment, the lower handle 64 is designed with a channel 71 that has a groove along its sidewalls for this purpose. As seen in FIG. 9c, the proximal end of the lower handle 64 is shown with a cross-section view shown in FIG. 9d to depict the channel 71. The lower handle 64 has sidewalls 170 and lower wall 172. Grooves 174 are cut along at least a portion of the length of the lower handle 64. As seen in FIG. 9e, the slider 90 rides along the lower handle 64. As seen in the cross-section view in FIG. 9f, the slider 90 (with hole 182 for fastener 91) preferably is designed to have a lip portion 184 that is configured to fit within the channel 71 of the lower handle 64 with desirably low tolerance such that it slides easily, but does not twist or rotate under force. The lip portion 184 has side walls 176 and bottom wall 178. The side walls 176 have tongue portions 180 that are designed to fit within the grooves 174.

Figure 10:
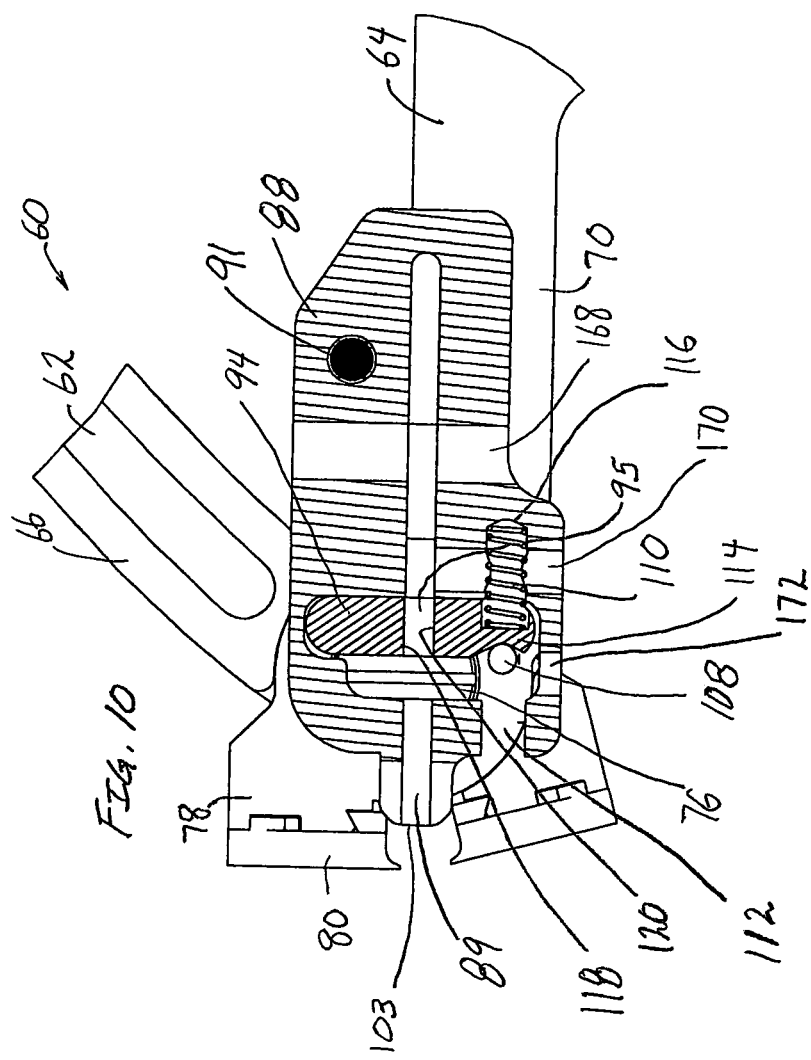
FIG. 10 is a partial cross section view of the distal end of one embodiment of the securing device.
Figure 11:
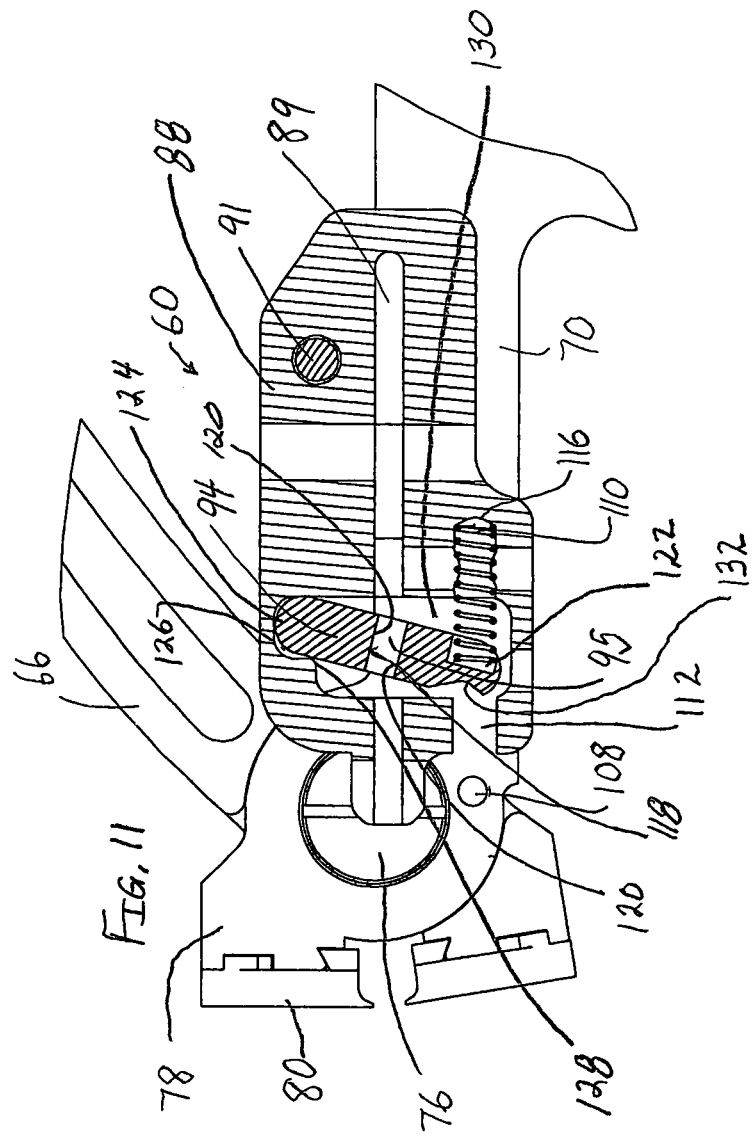
FIG. 11 is a partial cross section view of the distal end of one embodiment of the securing device.

A preferred embodiment for the gripping block design is shown in FIG. 10. In its open position, the handles 62, 64 of the securing device 60 are biased open by a means for biasing the handles in an open position, which is preferably a return spring 102 that urges the tensioning linkage 98 distally and thus opens the handles by way of the linkage 105. In its fully open position, the device 60 has the gripping block 88 fully advanced distally and the cutting blades 80 are fully opened. In the open position, the slot 95 of the slotted plate 94 is in alignment with the groove 89 opening in the gripping block 88. The slotted plate 94 as shown has an upper inner surface 118 and a lower inner surface 120 defining the slot 95. Perhaps as best seen in FIG. 11, the slotted plate 94 is housed within a chamber 130.

In this opened position shown in FIG. 10, the post 16 of the clamp 10 can readily fit within the groove 89 and through the slot 95 in the slotted plate 94. The gripping means is constructed with a means for inactivating the gripping function of the gripping means. In the preferred embodiment shown, the slotted plate 94 is maintained in this open position by pin 108, which is preferably formed integral with the head 78 of the upper handle 62 and extends outward from the surface of the head 78. The gripping block 88 preferably has a groove 112 formed along the distal end of its inside surface 92 to allow for the pin 108 to enter into the distal end of the gripping block 88. As the gripping block 88 slides distally forward, the pin 108 contacts the lower end 114 of the slotted plate 94 and forces the slotted plate to its open position. There is preferably an indent 132 on the lower end 114 of the slotted plate 94 to receive the pin 108. The gripping means also has a means for activating the gripping function of the gripping means. In the preferred embodiment shown, there is a spring 110, which has its proximal end housed within a cavity 116 of the gripping block 88. The distal end of the spring 110 is housed within a recess 122 in the lower end of the slotted plate. When the gripping block 88 is moved proximally away from the pin 108, the spring 110 activates the gripping function by rotating the slotted plate 94 as explained below.

The securing device 60 has a means for activating the tension assembly when the handles are brought together. As shown for the preferred embodiment, a linkage 105 is connected to the upper handle 62 by having its upper end 142 having a hole through which a fastener 106 can be inserted with the fastener passing through hole 166 in flange 164 of the handle 62. The linkage 105 thus has a pivot point about the upper handle 62. The linkage 105 is also connected to the tension linkage 98 in a similar manner. The lower end 140 of the linkage has a hole through which a fastener 106 is passed where the fastener 106 also is passed through the hole 138 defined in flanges 139 of the tension linkage 98 (see FIG. 12). The linkage 105 thus also has a pivot point about the lower handle 64.

When the handles 62, 64 are forced together, the linkage 105 will cause the tension linkage 98 to move or ride proximally within the channel 71 of the lower handle 64. The tension linkage 98 will thus elongate the tension spring 97 and cause the slider 90 to move or slide proximally. The gripping block 88, being connected to the slider 90 will also move proximally as reflected in FIG. 11. The movement of the gripping block 88 proximally causes the slotted plate 94 to disengage the pin 108, and thus spring 110 forces the lower end 114 of the slotted plate 94 to move distally. This movement causes the slot 95 to rotate out of alignment with the groove 89 in the gripping block 88, and thus when the post 16 of the clamp 10 is in the groove 89, the post 16 will be held by friction by the inner surfaces 118, 120 of the slotted plate 94. To assist in the rotation of the slotted plate 94 the upper end 124 of the plate is housed within a recess 126 within the gripping block 88, which recess 126 allows the plate 94 to pivot about the recess lip 128.

The gripping block 88 can be designed with vent holes to reduce weight and to improve cleansing and sterilization. For example, as shown in FIG. 10, vent holes 168, 170, 172 are formed within the gripping block 88 by machining either partially or completely through the gripping block 88.

There are various embodiments that can be used for various aspects of the securing device 60 described herein. The gripping block can be designed with other means for gripping the post 16. For example, instead of having the post 16 designed to fit within the gripping block 88, the gripping block 88 can be designed with gripping means on its surface. For example, pinchers can be provided on the outer surface of the gripping block 88, with the pinchers being activated by either the action of the handles or by manually closing the pinchers onto the post 16 prior to activating the handles.

Also, the tension assembly 100 can be constructed using different mechanical features that are all designed to exert a proximally-acting pulling force or tensioning force to the post 16 as it is firmly held by the gripping block 88 when a closing force is applied to the handles.

One example for the tension assembly 100 is depicted in FIG. 12. In this embodiment, the slider 90 is connected at its proximal end 96 to the tension spring 97 by way of a threaded end 134. The threaded end 134 is designed such that the threads match to the diameter of the metal rod for the spring 97. Similarly, the distal end 137 of the tension linkage 98 also has a threaded end 136 for securing the distal end of the spring 97. The tension linkage 98 has flanges 139 defining a hole 138 for being secured to the linkage 105 that has a mating lower end 140 with a hole such that the pin 106 can be used to secure the linkage 105 to the tension linkage 98.

In another embodiment for the tension assembly 100, depicted in FIG. 13, the slider 90 is connected at its proximal end 96 to the spring 97 by having a hook 144 on the distal end of the spring 97 that is retained by fastener 150, which is received through a hole 151 in the slider 90. Similarly, the proximal end of the spring 97 is secured to the distal end 137 of the tension linkage 98 by having a hook 144 on the proximal end of the spring 97 that is retained by fastener 152, which is received through a hole 153 in the tension linkage 98. Preferably, the slider 90 and the tension linkage 98 have channels 146, 140 defined by walls 148, 140, respectively, to reduce weight for the device and so that the state of the spring can be visualized, and also to aid in sterilization and ventilation. The tension linkage 98 also preferably has a tongue 186 extending along its length such that it can slide within the channel 71 of the lower handle 64 in a similar fashion as described with respect to the slider 90.

Another embodiment for the tension assembly 100 is depicted in FIG. 14. In this embodiment, the proximal end of the tension spring 97 is secured to the distal end 137 of the tension linkage 98 as before. In this embodiment, the spring 97 preferably can be a machined helix spring that is either welded to the tension linkage 98 or formed integrally therewith by machining, electrical discharge machining, laser cutting, or water jet cutting. At its distal end the spring 97 is connected to a slider 156 having a hole 158 in its top surface that is used to secure the spring 97 to the slider 90. As shown, the slider 90 has a bore 162 defining a hole 160 through the top surface of the slider 90 through the bottom surface of the slider 90. A fastener 154 is used to secure the slider 90 to the slider 156. In this embodiment, the slider 90 is formed integral to the gripping block 88, such as by way of a casting or machining operation.

The tension assembly can also be an elastic material. For example, an elastic band material can be used instead of a spring.

The securing device 60 is used to secure the cranial clamp 10 to the skull 38 and, for example, bone flap 36 (see FIG. 4-5). For example, as shown in FIG. 4, the clamp 10 is inserted between the skull 38 and bone flap 36 and the top member 14 is slid down the post 16 to adjacent the outer surface 46 of the skull 38. As shown in FIG. 15, the securing device 60 is then fit over the post 16 by guiding the post 16 into the groove 89 in the gripping block 88 as seen in FIG. 16. As seen in FIG. 16, when the securing device 60 is in its open position with the handles 62, 64 opened, the post 16 rests within groove 89 of the gripping block 88. The heads 78 of the handles 62, 64 are spread apart to allow the post to enter between the opposing edges 79 of the blades 80.

As seen in FIG. 17, in the open position, the post 16 can slide freely in and out of the groove 89 in the gripping block 88. The pin 108 serves to hold the slotted plate 94 back against the spring 110 such that the slot 95 in the slotted plate 94 is in alignment with the groove 89 to permit the post 16 to slide in and out of the securing device 60.

As seen in FIGS. 7 and 18, as the handles 62, 64 are brought together, the tension spring 97 is elongated causing the slider 90 to be pulled proximally along the lower handle 64, thereby causing the gripping block 88 to also slide proximally as well. This movement causes the spring 110 in the gripping block to push the lower end 114 of the slotted plate 94 forward because it is no longer held in place by pin 108. This causes the slotted plate 94 to rotate or pivot within the cavity 130 about recess lip 128, and to engage and secure the post 16. As more pressure is applied to the handles, the tension spring 97 causes the slider 90 and gripping block 88 to move (slide) proximally while still retaining the post 16 within the slotted plate 94. This action also causes the lower member 12 to be pulled snugly against the lower surfaces 40, 42 of the bone flap 36 and skull 38, and thereby also causes the outer surfaces of the skull and bone flap 44, 46 to be snugly fit against the upper member 14 with the blades 80 forcing against the upper member 14. It is preferred to have the distal end of the securing device 60 relatively close the upper member 14 at the beginning of the process so that the force exerted upon the handles is translated into tension energy to the post 16 to ensure a tight hold on the skull and bone flap 36, 38 instead of having that energy used to pull the post 16 proximally to achieve the tight fit. In the preferred embodiment, it is desired that the cutting edge 79 of the blades 80 be no more than 20 mm, more preferably no more than 15 mm, even more preferably no more than 10 mm, and most preferably no more than 5 mm from the outer surfaces 44, 46 of the skull and bone flap when the securing device 60 is first positioned.

When enough force is applied to the handles 62, 64 the cutting edge 79 of the cutting blades 80 cut the post 16 as depicted in FIG. 19. Preferably, the cutting edges 79 are designed to first deform the tubular shape of the post 16, and thereafter shear and/or cut the post 16; in this way, the deformed post 16 at the cut section has a different geometry than the opening 32 in the upper member 14 and thus the clamp 10 is retained in position. The sheared off section of the post 16 can then be removed from the securing device 60 by releasing the handles 62, 64 and allowing the pin 108 to force the lower end 114 of the slotted plate 94 back against the spring 110, which action will align the slot 95 of the slotted plate 94 with the groove 89 of the gripping block 88 and release the post 16.

Thus, the actuation of the handles causes a proximally-acting pulling force to be exerted onto the post 16. This force acts to pull the lower member 12 proximally and to firmly plant the members 12, 14 of the cranial clamp 10 by way of tension along the shaft of the post 16. The securing device 60 is substantially perpendicular to the skull during the process, which location does not exert substantially any force to the post 16 in a direction perpendicular to the longitudinal axis of the post 16. A beneficial feature of the present invention is that the securing or gripping of the post 16 and the subsequent shearing/cutting of the post 16 is in one uniform movement—that is, a physician can conduct the process by simply squeezing the handles together in one uniform motion without having to first actuate the handles to achieve a proper grip on the post 16 and thereafter in a second, separate motion apply a force to shear/cut the post 16 as with previous devices.

The securing device 60 is preferably made of materials that can undergo repeated sterilization processes. For example, the securing device 60 can be made from stainless steel, titanium, a titanium alloy, composite, polymer, or a combination thereof.

The invention described and claimed herein is not to be interpreted as being limited to the embodiments described above to illustrate the preferred embodiments. Equivalent embodiments are also intended to be within the scope of the present invention. Various modifications to the invention in addition to those shown and described herein will become apparent to those skilled in the art after reading the description provided.

What is claimed:

1. A securing device configured to secure a fixation device having an elongated section, the securing device comprising:
   a first handle and a second handle that is pivotably attached to the first handle, the first and second handles each defining a distal end and a proximal end spaced from the respective distal end in a proximal direction;
   a cutting blade, affixed at the distal end of the second handle, the cutting blade configured to cut the elongated section of the fixation device as the first and second handles are further brought together, wherein the distal end of the second handle is disposed closer to the cutting blade than the proximal end of the second handle;
   a gripping member moveably connected to the second handle, the gripping member includes a plate that defines a slot configured to receive the elongated section of the fixation device, the gripping member configured to grip the elongated section of the fixation device in a secure manner; and
   a tensioning element configured to exert a force acting in the proximal direction on the gripping member, where the tensioning element biases the gripping member to move in the proximal direction along the second handle such that the plate rotates and secures the elongated section of the fixation device in the slot as the gripping member moves in the proximal direction so as to induce tension in the elongated section of the fixation device as the first and second handles are brought together in a first motion.

2. The securing device of claim 1 wherein the gripping member is slidably connected to the second handle.

3. The securing device of claim 1 wherein the gripping member has an elongated groove dimensioned to accept the elongated section of the fixation device.

4. The securing device of claim 1 further comprising a stop configured to prevent the gripping member from gripping the elongated section of the fixation device when the first and second handles are in an open position.

5. The securing device of claim 1 further comprising a linkage configured to activate a gripping ability of the gripping member when the first and second handles are brought together.

6. The securing device of claim 1, wherein the cutting blade is a first cutting blade, wherein the securing device further comprises a second cutting blade affixed at the distal end of the first handle, wherein uniform motion of the first and second handles from an open position toward a closed position causes the gripping member to secure the elongated section of the fixation device, then causes the tensioning element to exert the force acting in the proximal direction on the gripping member so as to place the elongated section of the fixation device in tension, and then causes the first and second cutting blades to cut the elongated section of the fixation device.

7. The securing device of claim 6, further comprising a spring configured to bias the first and second handles toward the open position.

8. The securing device of claim 6, wherein the movement of the first and second handles toward the closed position causes the first and second cutting blades to first deform the elongated section of the fixation device prior to cutting the elongated section of the fixation device.

9. The securing device of claim 1, wherein the gripping member further comprises a spring member that biases the plate to rotate as the gripping member moves in the proximal direction.

10. The securing device of claim 1, wherein the tensioning element is a spring.

11. The securing device of claim 1, wherein the cutting blade is a first cutting blade, the securing device further comprising a second cutting blade affixed at the distal end of the first handle, the second cutting blade configured to cut the elongated section of the fixation device as the first and second handles are further brought together, wherein the distal end of the first handle is disposed closer to the second cutting blade than the proximal end of the first handle.

12. A securing device configured to secure a fixation device having an elongated section, the securing device comprising:
   a first handle and a second handle that is pivotably attached to the first handle, the first and second handles each defining a distal end and a proximal end spaced from the respective distal end in a proximal direction;
   a gripping member having an outer surface and a proximal portion, the gripping member being moveably connected with one of the first and second handles so as to move in the proximal direction when the first and second handles are brought together, wherein the gripping member includes a plate that defines a slot, such that the slot of the plate is configured to receive the elongated section of the fixation device, and the plate is configured to rotate as the gripping member moves in the proximal direction so as to secure the elongated section of the fixation device with respect to the gripping member;
   a tensioning element having a distal end and a proximal end, the distal end of the tensioning element being connected to the proximal portion of the gripping member, and the proximal end of the tensioning element being connected to a linkage that joins the other of the first and second handles to the handle to which the gripping member is connected, such that the tensioning element causes the gripping member to move when the first and second handles are brought together, and a cutting blade, affixed at the distal end of the first handle, such that the distal end of the first handle is disposed closer to the cutting blade than the proximal end of the first handle;

wherein pivoting the first and second handles relative to each other causes the gripping member to grip the elongated section of the fixation device and to move in the proximal direction and causes the cutting blade to cut the elongated section of the fixation device.

13. The securing device of claim 12 wherein the gripping member is slidably connected to the second handle, and the pivoting of the first and second handles relative to each other causes the gripping member to slide in the proximal direction along the second handle.

14. The securing device of claim 13 wherein the slot of the plate is aligned with an internal channel of the gripping member when the first and second handles are in an open position.

15. The securing device of claim 14, further comprising a pin located on the second handle to block rotational movement of the slotted plate, wherein the pin is removed from blocking the rotational movement of the slotted plate as the first and second handles are brought together.

16. The securing device of claim 13 wherein the tensioning element is a spring.

17. The securing device of claim 13 wherein the second handle includes a channel defined by a first sidewall, an opposing sidewall, and a bottom wall.

18. The securing device of claim 17 wherein the channel includes a groove extending along at least a portion of the sidewalls of the second handle.

19. The securing device of claim 18 wherein the gripping member includes a tongue portion dimensioned to fit within the groove of the channel in the second handle.

20. The securing device of claim 13, wherein the cutting blade is a first cutting blade, the securing device further comprising a second cutting blade affixed at the distal end of the second handle, the second cutting blade configured to cut the elongated section of the fixation device as the first and second handles are further brought together, wherein the distal end of the second handle is disposed closer to the second cutting blade than the proximal end of the second handle.

21. The securing device of claim 12, further comprising a spring located within the gripping member to rotate the slotted plate.

22. The securing device of claim 12, wherein the gripping member has an internal channel dimensioned to receive the elongated section of the fixation device such that the elongated section extends into the slot of the plate.

23. The securing device of claim 22 wherein the internal channel is an elongated groove.

24. The securing device of claim 12, wherein the cutting blade is a first cutting blade affixed to the first handle, and the securing device further comprises a second cutting blade affixed at the distal end of the second handle, such that the distal end of the second handle is disposed closer to the cutting blade than the proximal end of the second handle.

25. The securing device of claim 12, wherein the cutting blade is a first cutting blade, the securing device further comprising a second cutting blade affixed at the distal end of the second handle, the second cutting blade configured to cut the elongated section of the fixation device as the first and second handles are further brought together, wherein the distal end of the second handle is disposed closer to the second cutting blade than the proximal end of the second handle.

* * * * *